US012638459B2

(12) United States Patent
Young et al.

(10) Patent No.: US 12,638,459 B2
(45) Date of Patent: *May 26, 2026

(54) METHOD OF DIAGNOSING OVERACTIVE BLADDER DISORDER

(71) Applicant: University of Portsmouth Higher Education Corporation, Portsmouth (GB)

(72) Inventors: John Young, Fareham (GB); Sepinoud Firouzmand, Gunwharf Quays (GB)

(73) Assignee: University of Portsmouth Higher Education Corporation, Portsmouth (GB)

( * ) Notice: Subject to any disclaimer, the term of this patent is extended or adjusted under 35 U.S.C. 154(b) by 1119 days.

This patent is subject to a terminal disclaimer.

(21) Appl. No.: 17/426,058

(22) PCT Filed: Jan. 28, 2020

(86) PCT No.: PCT/GB2020/050194
§ 371 (c)(1),
(2) Date: Jul. 27, 2021

(87) PCT Pub. No.: WO2020/157485
PCT Pub. Date: Aug. 6, 2020

(65) Prior Publication Data
US 2022/0099685 A1 Mar. 31, 2022

(30) Foreign Application Priority Data
Jan. 29, 2019 (GB) ..................................... 1901186

(51) Int. Cl.
| | |
|---|---|
| *G01N 33/68* | (2006.01) |
| *A61K 31/137* | (2006.01) |
| *A61K 31/216* | (2006.01) |
| *A61K 31/222* | (2006.01) |
| *A61K 31/4025* | (2006.01) |
| *A61K 31/426* | (2006.01) |
| *A61K 31/445* | (2006.01) |

(Continued)

(52) U.S. Cl.
CPC ....... *G01N 33/6893* (2013.01); *A61K 31/137* (2013.01); *A61K 31/216* (2013.01); *A61K 31/222* (2013.01); *A61K 31/4025* (2013.01); *A61K 31/426* (2013.01); *A61K 31/445* (2013.01); *A61K 31/453* (2013.01); *A61K 31/46* (2013.01); *A61K 31/4725* (2013.01); *A61P 13/10* (2018.01); *G01N 33/5091* (2013.01); *G01N 33/5735* (2013.01); *G01N 33/944* (2013.01); *G01N 2333/5409* (2013.01); *G01N 2800/341* (2013.01)

(58) Field of Classification Search
None
See application file for complete search history.

(56) References Cited

U.S. PATENT DOCUMENTS

2010/0166739 A1 7/2010 Chancellor et al.

FOREIGN PATENT DOCUMENTS

| | | |
|---|---|---|
| JP | 2014500504 | 1/2014 |
| WO | 2011026891 | 3/2011 |

(Continued)

OTHER PUBLICATIONS

Abrams et al., "Urinary Urgency: A Review of its Assessment as the Key symptom of the Overactive Bladder Syndrome." World J Urol. Jun.;30(3):385-392 (2012).

(Continued)

*Primary Examiner* — Anna Skibinsky
*Assistant Examiner* — Joseph Pulliam
(74) *Attorney, Agent, or Firm* — SNELL & WILMER L.L.P.

(57) ABSTRACT

The invention provides a method of diagnosing overactive bladder disorder (OAB), the method comprising: measuring the concentrations of one or more of adenosine triphosphate (ATP), acetylcholine (ACh), nitric oxide (NO) and interleukin 5 (IL-5) in a sample obtained from a subject; normalising the concentrations to the concentration of creatinine (Cr) in the sample; range standardising the normalised concentrations and subject's age to the following values: Age to 120 years old; ATP/Cr to 0.000001; ACh/Cr to 0.1; NO to 20000; IL-5/Cr to 100; wherein the likelihood of having OAB ($p_{OAB}$)=$1/1+e^{-x}$, where X=one or more of the following: (a) (−2.688±1.050)+5.472±2.098×subject's age+1.356±0.559×Gender (Female=1, Male=0)+(−7.998±40.273)×[IL-5/Cr]; (b) (−2.141±0.966)+4.506±1.902×subject's age+1.034±0.519×Gender (Female=1, Male=0)+(−5294.063±9075.456)×[ACh/Cr]; (c) (−2.825±1.072)+5.964±2.167×subject's age+1.312±0.562×Gender (Female=1, Male=0)+17.790±58.762×[IL-5/Cr]+(−9180.821±12700.057)×[ACh/Cr]; (d) (−2.993±1.197)+5.580±2.309×subject's age+1.724±0.719×Gender (Female=1, Male=0)+63.571±73.444×[IL-5/Cr]+(−0908.523±13606.752)×[ACh/Cr]+(−566.991±636.589)×[ATP/Cr]; (e) (−3.090±1.200)+5.393±2.256×subject's age+1.797±0.717×Gender (Female=1, Male=0)+34.767±56.331×[IL-5/Cr]+(−562.743±629.316)×[ATP/Cr]; or (f) (−2.650±1.067)+5.516±2.120×subject's age+1.389±0.583×Gender (Female=1, Male=0)+(−4.060±45.238)×[IL-5/Cr]+(−1.456±6.833)×[NO/Cr]; and wherein a pOAB above a threshold indicates that the subject has a high likelihood of having or developing OAB and a pOAB below a threshold indicates that the subject does not have OAB.

6 Claims, 5 Drawing Sheets

(51) Int. Cl.

| | |
|---|---|
| *A61K 31/453* | (2006.01) |
| *A61K 31/46* | (2006.01) |
| *A61K 31/4725* | (2006.01) |
| *A61P 13/10* | (2006.01) |
| *G01N 33/50* | (2006.01) |
| *G01N 33/573* | (2006.01) |
| *G01N 33/94* | (2006.01) |

(56) References Cited

FOREIGN PATENT DOCUMENTS

| | | |
|---|---|---|
| WO | 2013188640 | 12/2013 |
| WO | 2016090168 | 6/2016 |
| WO | 2017073226 | 5/2017 |
| WO | 2019158937 | 8/2019 |

OTHER PUBLICATIONS

Abrams et al. (Eds) Incontinence 6th Edition. ICI-ICS. International Continence Society, Bristol UK, ISBN: 978-0956960733 (2017).

Digesu et al., "Overactive Bladder Symptoms: Do we Need Urodynamics?" Neurourology and Urodynamics;22:105-108. (2003).

Hashim et al., "Is the Bladder a Reliable Witness for Predicting Detrusor Overactivity?" The Journal of Urology.;175:191-194 (2006).

Irwin et al., "Worldwide Prevalence Estimates of Lower Urinary Tract Symptoms, Overactive Bladder, Urinary Incontinence and Bladder Outlet Obstruction." BJU Int.;108:1132-1138 (2011).

Lughezzani et al., "Comparison of the Diagnostic Accuracy of Micro-ultrasound and Magnetic Resonance Imaging/Ultrasound Fusion Targeted Biopsies for the Diagnosis of Clinically Significant Prostate Cancer." Eur Urol. 2(3):329-332. doi: 10.1016/j.euo.2018.10.001 (2019).

Valenberg et al., Prospective Validation of an mRNA-based Urine Test for Surveillance of Patients with Bladder Cancer. Eur Urol. 75; 853-860 (2019).

Pennycuff, J. et al., "Current concepts in urinary biomarkers for overactive bladder: what is the evidence?", Current Bladder Dysfunction Reports, 2017.

Yoon Seok Suh et al., "Potential biomarkers for diagnosis of overactive bladder patients: Urinary nerve growth factor, Prostaglandin E2, and adenosine triphosphate", International Neurology Journal, 2017.

Firouzmand, S et al., "New participant stratification and combination of urinary biomarkers and confounders could improve diagnostic accuracy for overactive bladder", Scientific Reports, 2020.

Masaki Yoshida et al., "Management of detrusor dysfunction in the elderly: changes in acetylcholine and adenosine triphosphate release during aging", Urology, 2004.

International Search Report and Written Opinion dated May 4, 2020 in PCT Application No. PCT/GB2020/050194.

First Substantive Examination Report dated Apr. 25, 2024 in AE Application No. P6001309/2021.

EPO Examination Report (Art. 94 EPC) dated Mar. 26, 2024 in respect of EP Application No. 20704344.9.

First Office Action issued Nov. 14, 2023 in JP Application No. 2021-544745.

Office Action issued Oct. 15, 2024 in KR Application No. 10-2021-7026991.

METHOD OF DIAGNOSING OVERACTIVE BLADDER DISORDER

CROSS REFERENCE TO RELATED APPLICATIONS

This application is a U.S. national stage entry under 35 U.S.C. § 371 of International Application No. PCT/GB2020/050194 filed Jan. 28, 2020, entitled "METHOD," which claims priority to, and the benefit of, Great Britain Patent Application Serial No. 1901186.5, filed on Jan. 29, 2019. Each of the foregoing applications are hereby incorporated by reference in their entirety (except for any subject matter disclaimers or disavowals, and except to the extent of any conflict with the disclosure of the present application, in which case the disclosure of the present application shall control).

FIELD OF INVENTION

The present invention relates to methods of diagnosing overactive bladder disorder (OAB), as well as methods of treatment and methods of monitoring disease progression. Computer systems and programs are also provided.

BACKGROUND TO THE INVENTION

Overactive bladder (OAB) is symptom syndrome characterised by urinary urgency, increased frequency, nocturia and, in some, urge incontinence. OAB affects approximately 1 in 5 adults with prevalence increasing with age. The nature of the urinary symptoms significantly impact sufferers' physical and mental health, social, sexual and professional lives. Estimates of economic burden vary, but a recent meta-analysis on US data reported per-patient annual costs of 656-860 USD in direct costs and >11,000 USD in indirect costs; the latter attributed to falls and fractures, comorbidities and work productivity impairment. These economic estimates are in line with a prediction for an annual global cost in 2018 of €3.2tn.

Given that the urinary symptoms that define OAB also present with LUT infection, metabolic and other diseases of the urinary tract, diagnosis centres on first excluding these diseases. Diagnostic guidelines therefore combine patient history, physical examination and urinalysis; with bladder diaries and questionnaires to score patients' symptoms mandated or recommended. Questionnaire-based diagnosis of OAB suffers from the issues of subjectivity and insensitivity. There is no consensus regarding the score or degree of bothersome required for positive diagnosis and OAB treatment.

Although argued that 'OAB with or without urgency incontinence [is] presumed to be detrusor overactivity' [Abrams et al. 2017], there is evidence that does not support this. In a study of 843 women (mean age 55, range: 22-73 years old) with OAB symptoms, only 54% had detrusor instability, and, amongst 1641 women with DO, only 28% had OAB symptoms [Digesu et al. 2003]. In another study [Hashim and Abrams] 10% of men and 42% of women with urgency and urgency incontinence did not exhibit urodynamically-proven DO, and 31% of men and 56% of women presenting with OAB without incontinence did not exhibit DO.

With OAB diagnosis being a capture-all for the combination of urgency, frequency, nocturia, with or without incontinence, and with no discriminatory means for positive diagnosis of OAB or even to rule out OAB, patients may be misclassified especially when they are at initial stages of symptom development, when they exhibit less severe albeit bothersome urinary symptoms. Therefore, there is an unmet need for a diagnostic tool that is non-invasive, highly sensitive and specific for OAB. While the significant effect of OAB treatment at improving health-related quality of life has been observed, it has been shown that around 76% of those diagnosed with OAB are left untreated, however, the frequency of medical treatment increases with age and with presence of OAB-associated comorbidities. Considering the clinical consequences of polypharmacy in elderly population and polypharmacy as one of the significant factors in early OAB treatment discontinuation, identification of population at risk of developing OAB would allow regular monitoring at early age, enabling early classification and treatment.

SUMMARY OF THE INVENTION

The present inventors have identified combinations of biomarkers and confounders (age, gender, etc.) that can be analysed using novel algorithms to determine the probability that a subject has or does not have overactive bladder disorder (OAB). Indeed, the novel algorithms have demonstrated particularly impressive accuracy in excluding OAB. In other words, the algorithms can be used to rule out OAB and thereby reduce or avoid unnecessary or inappropriate treatment. A particular advantage of the present invention is that the biomarkers can be obtained non-invasively, which can improve the patient experience and significantly reduce costs associated with making a diagnosis.

Accordingly, in a first aspect the present invention provides a method of diagnosing overactive bladder disorder (OAB), the method comprising:

measuring the concentrations of one or more of adenosine triphosphate (ATP), acetylcholine (ACh), nitric oxide (NO) and interleukin 5 (IL-5) in a sample obtained from a subject;

normalising the concentrations to the concentration of creatinine (Cr) in the sample;

range standardising the normalised concentrations and subject's age to the following values: Age to 120 years old; ATP/Cr to 0.000001; ACh/Cr to 0.1; NO to 20000; IL-5/Cr to 100;

wherein the likelihood of having OAB $(p_{OAB}) = 1/1 + e^{-x}$, where X=one or more of the following:

$$(-2.688 \pm 1.050) + 5.472 \pm 2.098 \times \text{subject's age} + 1.356 \pm 0.559 \times \text{Gender (Female=1,Male=0)} + (-7.998 \pm 40.273) \times [\text{IL-5/Cr}]; \quad (a)$$

$$(-2.141 \pm 0.966) + 4.506 \pm 1.902 \times \text{subject's age} + 1.034 \pm 0.519 \times \text{Gender (Female=1, Male=0)} + (-5294.063 \pm 9075.456) \times [\text{ACh/Cr}]; \quad (b)$$

$$(-2.825 \pm 1.072) + 5.964 \pm 2.167 \times \text{subject's age} + 1.312 \pm 0.562 \times \text{Gender (Female=1, Male=0)} + 17.790 \pm 58.762 \times [\text{IL-5/Cr}] + (-9180.821 \pm 12700.057) \times [\text{ACh/Cr}]; \quad (c)$$

$$(-2.993 \pm 1.197) + 5.580 \pm 2.309 \times \text{subject's age} + 1.724 \pm 0.719 \times \text{Gender (Female=1, Male=0)} + 63.571 \pm 73.444 \times [\text{IL-5/Cr}] + (-10908.523 \pm 13606.752) \times [\text{ACh/Cr}] + (-566.991 \pm 636.589) \times [\text{ATP/Cr}]; \quad (d)$$

$$(-3.090 \pm 1.200) + 5.393 \pm 2.256 \times \text{subject's age} + 1.797 \pm 0.717 \times \text{Gender (Female=1, Male=0)} + 34.767 \pm 56.331 \times [\text{IL-5/Cr}] + (-562.743 \pm 629.316) \times [\text{ATP/Cr}]; \text{ or} \quad (e)$$

3

$$(-2.650\pm1.067)+5.516\pm2.120\times\text{subject's age}+1.389\pm0.583\times\text{Gender (Female=1, Male=0)}+(-4.060\pm45.238)\times[\text{IL-5/Cr}]+(-1.456\pm6.833)\times[\text{NO/Cr}]; \quad\text{(f)}$$

and wherein a $p_{OAB}$ above a threshold indicates that the subject has a high likelihood of having or developing OAB and a $p_{OAB}$ below a threshold indicates that the subject does not have OAB.

Confounders used in the diagnostic methods of the invention include subject characteristics such as age and/or gender. Gender is coded for input to the algorithm, with 1 being female and 0 being male.

The biomarker concentrations are normalised to the concentration of urinary creatinine concentration, which is commonly used for biomarker standardisation. Creatinine is the breakdown product of creatinine phosphate metabolism of skeletal muscle tissue, which is filtered out of blood by kidneys and excreted in urine. Creatinine excretion is usually at a constant rate for an individual with a healthy renal function.

In preferred embodiments of the invention each independent variable is range standardised to the highest possible number that can be measured for any one subject (and even for some biomarkers the considered value was much higher), i.e., age is range standardized to 120 years old; ATP/Cr is range standardized to 0.000001; ACh/Cr is range standardized to 0.1; NO/Cr is range standardized to 20000; and IL-5/Cr is range standardized to 100. This ensures that any measured value can be range standardised to the same values used in the algorithms of the present invention.

Algorithms (a)-(f) of the diagnostic method of the invention have been shown to provide a clinically reliable diagnostic accuracy of OAB. The algorithms can also be used to make a negative diagnosis, i.e., to rule out or exclude OAB, and have been shown to have a particularly high negative predictive value (89-92%), indicating that they are particularly suited to ruling out OAB. By measuring the urinary levels of the associated biomarkers and entering the value(s) into one or more of algorithms (a)-(f) healthcare professionals can predict the probability of a subject having OAB at a much earlier stage in disease development and more accurately than the current invasive means of urodynamically-observed detrusor overactivity (DO). Importantly, the diagnostic method of the invention enables healthcare professionals to accurately and non-invasively exclude OAB in those patients with aetiologically distinct disease which have overlapping symptoms with OAB.

The outcome of the algorithm is a value of $p_{OAB}$. $p_{OAB}$ is compared to a threshold and a $p_{OAB}$ above a threshold indicates that the subject has a high likelihood of having or developing OAB, and a $p_{OAB}$ below a threshold indicates that the subject does not have OAB. A threshold level is typically determined from a relevant population of individuals who are free from OAB. The relevant population can be defined based on, for example, diet, lifestyle, age, gender, ethnic background or any other characteristic that can affect the normal levels of the markers. Once the threshold value is known, the measured $p_{OAB}$ value can be compared.

In embodiments of the invention the $p_{OAB}$ threshold is 0.5. Alternatively, $p_{OAB}$ thresholds may be optimised for maximum sensitivity or specificity or both. For example, optimal $p_{OAB}$ thresholds for maximum sensitivity and specify may be as follows: when X is (a): 0.51; when X is (b): 0.46; when X is (c): 0.46; when X is (d): 0.56; when X is (e): 0.56; or when X is (f): 0.51. This means that the test has the highest possible sensitivity and specificity at the same time. However, if sensitivity is the most important factor for the healthcare professional ordering or performing the test then other thresholds that have a higher sensitivity could be considered, but would have consequent lower specificity. Likewise, other thresholds could be used to maximise specificity, but would have consequent lower sensitivity.

$p_{OAB}$ thresholds for maximum sensitivity may be as follows when X is (a): 0.39; when X is (b): 0.41; when X is (c): 0.38; when X is (d): 0.35; when X is (e): 0.34; or when X is (f): 0.40. $p_{OAB}$ thresholds for maximum specificity may be as follows when X is (a): 0.80; when X is (b): 0.87; when X is (c): 0.80; when X is (d): 0.81; when X is (e): 0.81; or when X is (f): 0.80.

In preferred embodiments of the invention the sample is a urine sample. The sample can therefore be obtained non-invasively. This can significantly improve the patient experience compared to conventional diagnostic techniques relying on invasive urodynamics, especially where repeated assessments are required. The methods of the present invention can also significantly reduce costs associated with making a diagnosis of OAB by avoiding the need for the specialist equipment and skilled operators need for urodynamic assessments. By using a non-invasively obtained sample the diagnostic methods of the present invention can also enable diagnosis of OAB in patient groups for which current diagnostic methods are not suitable, such as the frail or elderly.

The subject is typically a mammal and is preferably a human. In embodiments of the invention the subject may be a paediatric or geriatric subject.

The biomarkers may be proteins, nucleic acids or biomolecules. Concentrations of the biomarkers can be measured using in vitro diagnostic platforms such as antibody-based platforms or RNA aptamer-based platforms or a combination thereof.

Diagnostic methods of the invention may further comprise administering a therapeutic agent to a subject diagnosed as having OAB. Accordingly, the present invention provides a method of treating OAB, the method comprising diagnosing OAB in a patient using the methods described herein, and administering a therapeutic agent to the patient. As mentioned above, the diagnostic methods of the present invention are non-invasive (and therefore likely to be more acceptable to a patient and potentially cheaper than an alternative invasive procedure), which can allow OAB to be diagnosed an earlier stage. This may provide an improved outcome when treating the diagnosed OAB, as at later stages of the disease the symptoms appear to be only partially reversible.

Therapeutic agents for treating OAB are known in the art and include antimuscarinic drugs and a β3 adrenergic receptor agonists. An antimuscarinic drug may be selected from one or more of darifenacin, oxybutynin, tolterodine, solifenacin, trospium, flavoxate, propiverine or fesoterodine. A β3 adrenergic receptor agonist may be mirabegron.

In a further aspect the present invention provides a method of monitoring the progression of OAB, the method comprising measuring first and second $p_{OAB}$ values according to the diagnostic methods described herein, wherein the first and second $p_{OAB}$ values are obtained from first and second samples obtained from a subject having or suspected of having OAB. Monitoring disease progression also allows the effectiveness of OAB treatments to be monitored, for example, stage-specific responses to treatment may be monitored.

The first and second samples may be obtained at an interval of at least two weeks.

In this aspect of the invention the first $p_{OAB}$ value and/or second $p_{OAB}$ value may be compared to a projected $p_{OAB}$ value, established by testing the same subject at an earlier date and predicating the $p_{OAB}$ value that is likely to be observed if OAB progresses and/or if treatment of OAB is successful. The prediction may simply be an increase or decrease in the $p_{OAB}$ value, or it may be possible to quantify the likely change.

The present invention additionally provides a computer system comprising processing means/a processor configured to execute instructions for:

receiving measured concentrations of one or more of adenosine triphosphate (ATP), acetylcholine (ACh), nitric oxide (NO), interleukin 5 (IL-5) and creatinine (Cr);

normalising the concentrations of ATP, ACh, NO and IL-5 to the concentration of Cr;

range standardising the normalised concentrations and subject's age to the following values: Age to 120 years old; ATP/Cr to 0.000001; ACh/Cr to 0.1; NO to 20000; IL-5/Cr to 100;

calculating x according to one or more of the following formulae:

$$X=(-2.688\pm1.050)+5.472\pm2.098\times\text{subject's age}+\\1.356\pm0.559\times\text{Gender (Female=1, Male=0)}+(-\\7.998\pm40.273)\times[\text{IL-5/Cr}]; \quad\quad (a)$$

$$X=(-2.141\pm0.966)+4.506\pm1.902\times\text{subject's age}+\\1.034\pm0.519\times\text{Gender (Female=1, Male=0)}+(-\\5294.063\pm9075.456)\times[\text{ACh/Cr}]; \quad\quad (b)$$

$$X=(-2.825\pm1.072)+5.964\pm2.167\times\text{subject's age}+\\1.312\pm0.562\times\text{Gender (Female=1, Male=0)}+\\17.790\pm58.762\times[\text{IL-5/Cr}]+(-\\9180.821\pm12700.057)\times[\text{ACh/Cr}]; \quad\quad (c)$$

$$X=(-2.993\pm1.197)+5.580\pm2.309\times\text{subject's age}+\\1.724\pm0.719\times\text{Gender (Female=1, Male=0)}+\\63.571\pm73.444\times[\text{IL-5/Cr}]+(-\\10908.523\pm13606.752)\times[\text{ACh/Cr}]+(-\\566.991\pm636.589)\times[\text{ATP/Cr}]; \quad\quad (d)$$

$$X=(-3.090\pm1.200)+5.393\pm2.256\times\text{subject's age}+\\1.797\pm0.717\times\text{Gender (Female=1, Male=0)}+\\34.767\pm56.331\times[\text{IL-5/Cr}]+(-562.743\pm629.316)\times\\[\text{ATP/Cr}];\text{ or} \quad\quad (e)$$

$$X=(-2.650\pm1.067)+5.516\pm2.120\times\text{subject's age}+\\1.389\pm0.583\times\text{Gender (Female=1, Male=0)}+(-\\4.060\pm45.238)\times[\text{IL-5/Cr}]+(-1.456\pm6.833)\times[\text{NO/}\\\text{Cr}];\text{ and} \quad\quad (f)$$

using X to calculate the likelihood of the subject having OAB ($p_{OAB}$) using the formula $p_{OAB}=1/1+e^{-x}$.

The present invention additionally provides a computer program comprising instructions which, when executed by a processor/processing means cause the processor/processing means to:

receive measured concentrations of one or more of adenosine triphosphate (ATP), acetylcholine (ACh), nitric oxide (NO), interleukin 5 (IL-5) and creatinine (Cr);

normalise the concentrations of ATP, ACh, NO and IL-5 to the concentration of Cr;

range standardise the normalised concentrations and subject's age to the following values: Age to 120 years old; ATP/Cr to 0.000001; ACh/Cr to 0.1; NO to 20000; IL-5/Cr to 100; and

calculate X according to one or more of the following formulae:

$$X=(-2.688\pm1.050)+5.472\pm2.098\times\text{subject's age}+\\1.356\pm0.559\times\text{Gender (Female=1, Male=0)}+(-\\7.998\pm40.273)\times[\text{IL-5/Cr}]; \quad\quad (a)$$

$$X=(-2.141\pm0.966)+4.506\pm1.902\times\text{subject's age}+\\1.034\pm0.519\times\text{Gender (Female=1, Male=0)}+(-\\5294.063\pm9075.456)\times[\text{ACh/Cr}]; \quad\quad (b)$$

$$X=(-2.825\pm1.072)+5.964\pm2.167\times\text{subject's age}+\\1.312\pm0.562\times\text{Gender (Female=1, Male=0)}+\\17.790\pm58.762\times[\text{IL-5/Cr}]+(-\\9180.821\pm12700.057)\times[\text{ACh/Cr}]; \quad\quad (c)$$

$$X=(-2.993\pm1.197)+5.580\pm2.309\times\text{subject's age}+\\1.724\pm0.719\times\text{Gender (Female=1, Male=0)}+\\63.571\pm73.444\times[\text{IL-5/Cr}]+(-\\10908.523\pm13606.752)\times[\text{ACh/Cr}]+(-\\566.991\pm636.589)\times[\text{ATP/Cr}]; \quad\quad (d)$$

$$X=(-3.090\pm1.200)+5.393\pm2.256\times\text{subject's age}+\\1.797\pm0.717\times\text{Gender (Female=1, Male=0)}+\\34.767\pm56.331\times[\text{IL-5/Cr}]+(-562.743\pm629.316)\times\\[\text{ATP/Cr}];\text{ or} \quad\quad (e)$$

$$X=(-2.650\pm1.067)+5.516\pm2.120\times\text{subject's age}+\\1.389\pm0.583\times\text{Gender (Female=1, Male=0)}+(-\\4.060\pm45.238)\times[\text{IL-5/Cr}]+(-1.456\pm6.833)\times[\text{NO/}\\\text{Cr}];\text{ and} \quad\quad (f)$$

use X to calculate the likelihood of the subject having OAB ($p_{OAB}$) using the formula $p_{OAB}=1/1+e^{-x}$.

The present invention additionally provides a computer readable medium comprising the computer program described herein. Typically the machine readable medium is a non-transitory medium or a storage medium, especially a non-transitory storage medium.

The present invention can therefore be used to provide a point-of-care diagnostic test, which utilises a non-invasively obtained sample to quickly and easily diagnose and/or monitor OAB.

BRIEF DESCRIPTION OF THE DRAWINGS

The invention will now be described in detail, by way of example only, with reference to the figures.

7

ACh+ATP. (E) Combination 17=Age+Gender+IL-5+ATP. (F) Combination 18=Age+Gender+IL-5+NO. AUC=Area under the ROC curve; Black diagonal solid line=prediction model curve; Grey diagonal dashed line=chance line.

Figure 5:
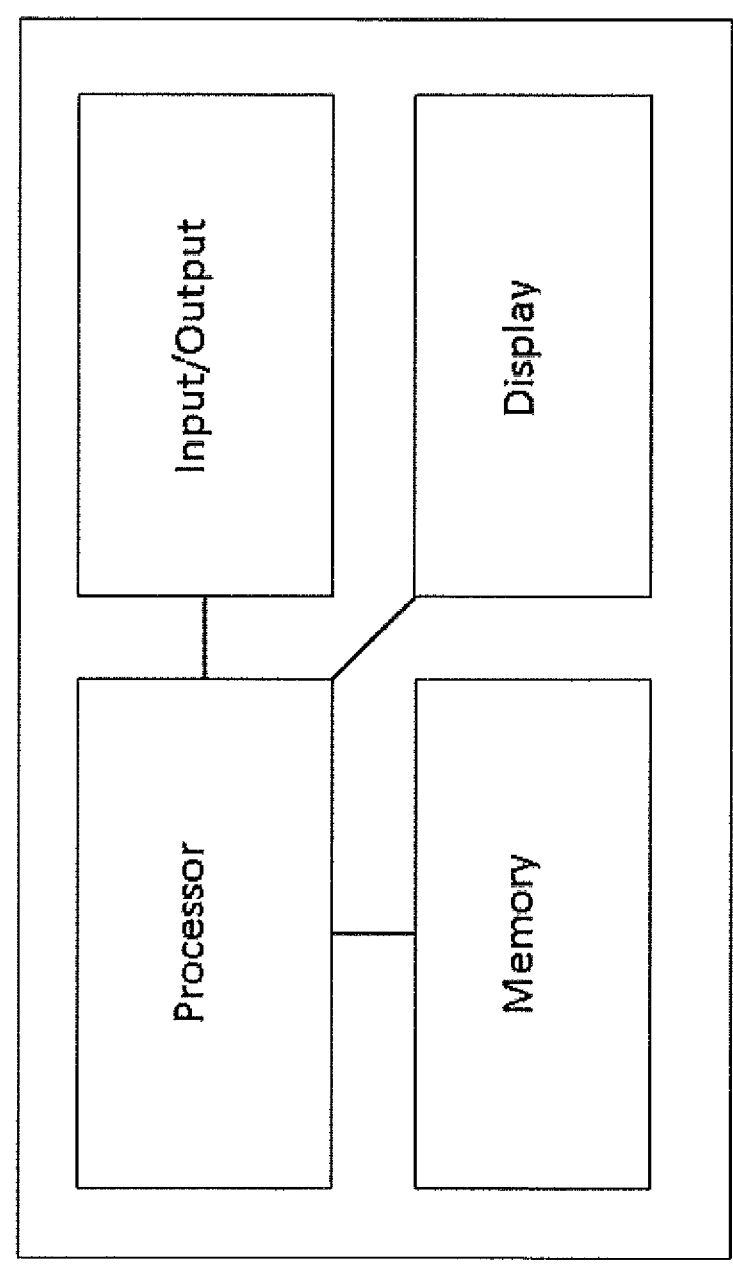

FIG. 5 shows a schematic illustration of a computer system configured to execute a computer program in line with the present invention. A computer [outer box] is shown. The computer is configured to execute a computer program to carry out the diagnostic method as described herein. The computer contains a processor, a memory, a display and an input/output for receiving data and/or outputting data.

EXAMPLES

Materials and Methods

Recruitment of Participants

This study and all its procedures were approved by the National Research Ethics Service (NRES) Committee South Central Berkshire (REC reference: 13/SC/0501). A total of 113 volunteer participants were recruited via volunteer sampling from the staff and students of the University of Portsmouth (UoP) and from the residents of The Briars Greensleeves Homes Trust, Isle of Wight; The National Federation of Women's Institutes; Portsmouth and Portsmouth Pensioners' Association. Participants were asked to complete International consultation on incontinence questionnaire-overactive bladder (ICIQ-OAB) questionnaire and to provide a fresh midstream urine sample. Collected samples and data were made anonymous using an ID code system.

Inclusion Criteria

Male or female participants aged and able to give informed consent for participation in the study.

Exclusion Criteria

Male or female participants aged 18; unable to give informed consent; diagnosed with neurologic disease (stroke, MS, Parkinson's disease, spinal cord injury); have history of uterine, cervical, vaginal or urethral cancer; history of cyclophosphamide use or any type of chemical cystitis; history of benign or malignant bladder tumours; have had Botulinum toxin injections, neuromodulation or augmentation cystoplasty.

Urine Pathology Tests

Pathology tests including microscopic, chromogenic UTI medium and dipstick urinalysis tests were immediately performed on a small proportion of each collected urine sample. Any positive test meant that a sample was considered 'unhealthy' and excluded from the study. The remainder of the urine sample was centrifuged (at 4000 rpm, 10 mins, at 4° C.) to separate into cell pellet and supernatant and stored separately at −80° C.

Biomarker Assays

The urinary (cell-free) concentrations of the candidate biomarkers were measured using ENLITEN® ATP Assay System Bioluminescence Detection Kit (FF2000, Promega, UK); Amplex® Red Acetylcholine/Acetylcholinesterase assay (Invitrogen™ Molecular Probes™, A12217, UK); Sievers Nitric Oxide Analyser (NOA™ 280i, Analytix, UK); BD OptEIA™ human MCP-1 enzyme-linked immunosorbent assay (ELISA) (559017, BD biosciences, UK); Quantikine® human IL-5 ELISA Kit (R&D Systems®, D5000B, UK) and the OptEIA™ Human IL-5 ELISA Set (555202, BD biosciences, UK) according to the manufacturers' instructions.

8

Creatinine Assay

All urinary biomarker values were normalized to urinary creatinine (Cr) concentrations. Creatinine was measured using the Cayman Creatinine (urinary) Colourimetric Assay Kit (CAY500701, Cambridge Bioscience, UK), following the manufacturer's instructions.

Statistical Analysis

Cluster Analysis

TwoStep cluster analysis was performed using IBM SPSS statistics 22.0 on the data obtained from ICIQ-OAB questionnaire (data not shown). The distribution of responses to each question (symptom/bothersome measure) was range standardized on a 0 to 1 scale. The software was programmed to automatically identify a maximum number of 15 clusters. Cluster analysis was run on different aspects of data obtained from the ICIQ-OAB questionnaire in order to identify the best combination of urinary characteristic scores that could be used to classify OAB patients. This included classification based on data acquired from urinary symptom scores only (USSO), urinary bothersome scores only (UBSO) or urinary symptom scores plus associated bothersome scores (USCPABS).

Correlation Analysis

Spearman's rank correlation coefficient (GraphPad Prism 6 software) was used to assess the relationship between the candidate urinary biomarkers and participants' total urinary symptoms scores. In addition, correlation test (IBM SPSS statistics 22.0) was used to assess strength of the potential relationship of the independent variables with dependent variable (outcome/OAB symptomatic); and to assess the multicollinearity between independent variables (any two independent variables with an r value above 0.80 are considered inter-correlated).

Binary Logistic Regression

The ability of the candidate biomarkers, individually or in combination (in different combination settings and with confounders (age, gender, collected urine volume), in predicting the probability of someone being OAB symptomatic was studied using binary logistic regression test (IBM SPSS statistics 22.0). In this case, instead of standardising each variable to its highest available measured value in this study, each variable was range standardised to the highest possible number that could be measured for any one human (and even for some biomarkers the considered value was much higher) i.e. age was range standardized to 120 years old; volume was range standardized to 1000 ml of urine; and candidate biomarkers were range standardised to the following values: ATP/Cr to 0.000001, ACh/Cr to 0.1, NO/Cr to 20000, Nitrite to 200, MCP-1/Cr to 100 and IL-5/Cr to 100. In this way, any measured value in the future could be range standardized to the same values used in this study and consequently could be placed in the generated logit formulae to estimate the probability of the presence of OAB.

Receiver Operating Characteristic (ROC), Positive Predictive Value (PPV) and Negative Predictive Value (NPV) Analyses ROC curve analysis (IBM SPSS statistics 22.0) was used in order to evaluate the discriminatory power of the generated OAB prediction models using predicted probability (PRE) values generated by logistic regression analyses. A predictive model with area under the ROC curve (AUC≥0.7)

was considered to have clinically reliable diagnostic power. The optimal cut-off value of the predicted probability (pOAB) for each prediction equation was determined as the value with the maximum Youden Index (J=sensitivity+specificity−1). PPV and NPV of each OAB predictive equation was calculated based on the sensitivity and specificity at optimal cut-off value and based on an estimate of OAB prevalence of 20% [Irwin et al. 2011].

Results

Participants

Figure 1:
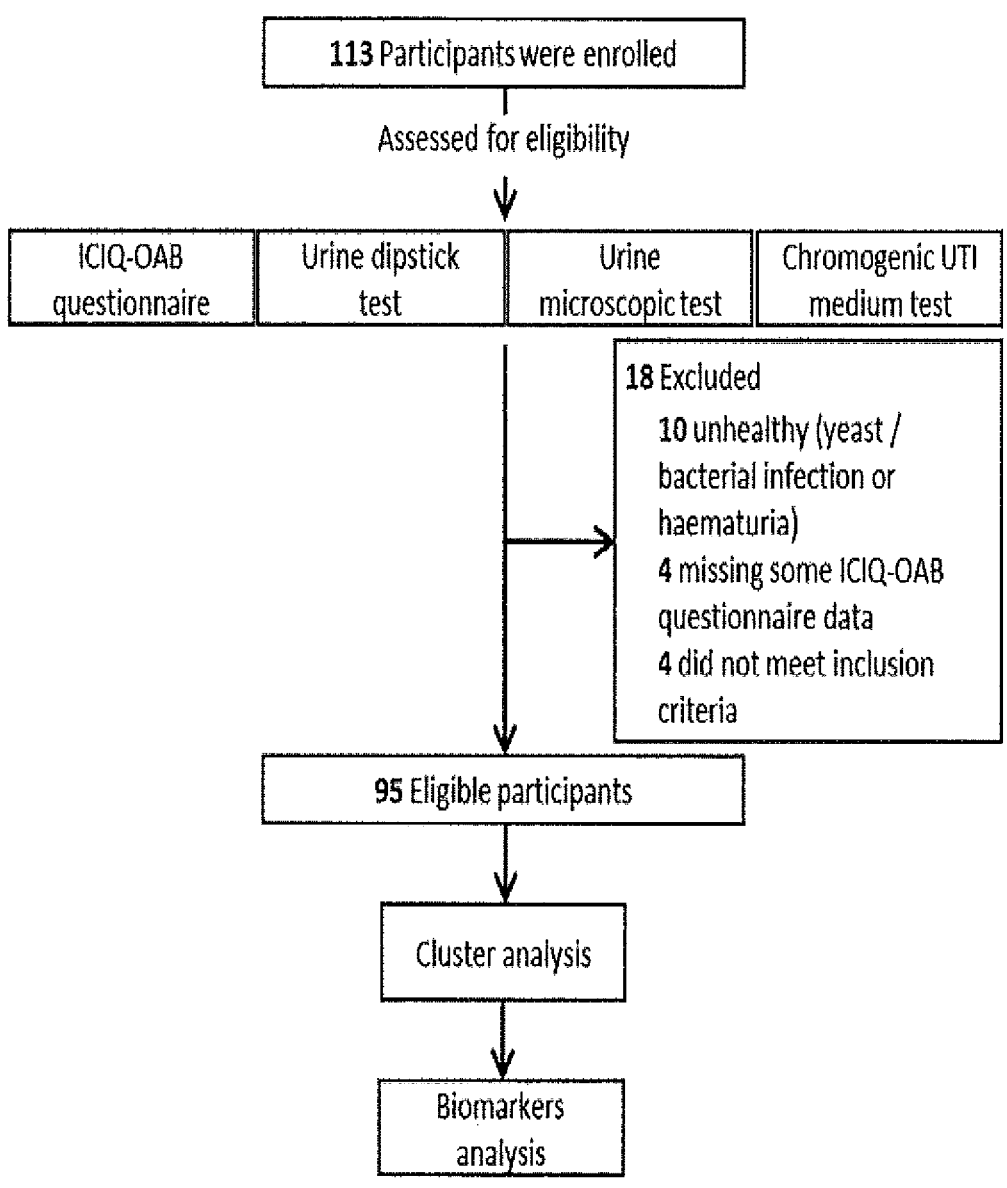
FIG. 1 shows a flow diagram of participants' selection. ICIQ-OAB=International consultation on incontinence questionnaire–overactive bladder.

Participants representing urinary symptoms similar to those of OAB were excluded from the analyses based on exclusion criteria and urinalysis tests. Out of 113 recruited participants, a total of 95 participants were eligible to be involved in the further analyses (FIG. 1).

Distribution of Urinary ICIQ-OAB Characteristic Scores

Figure 2:
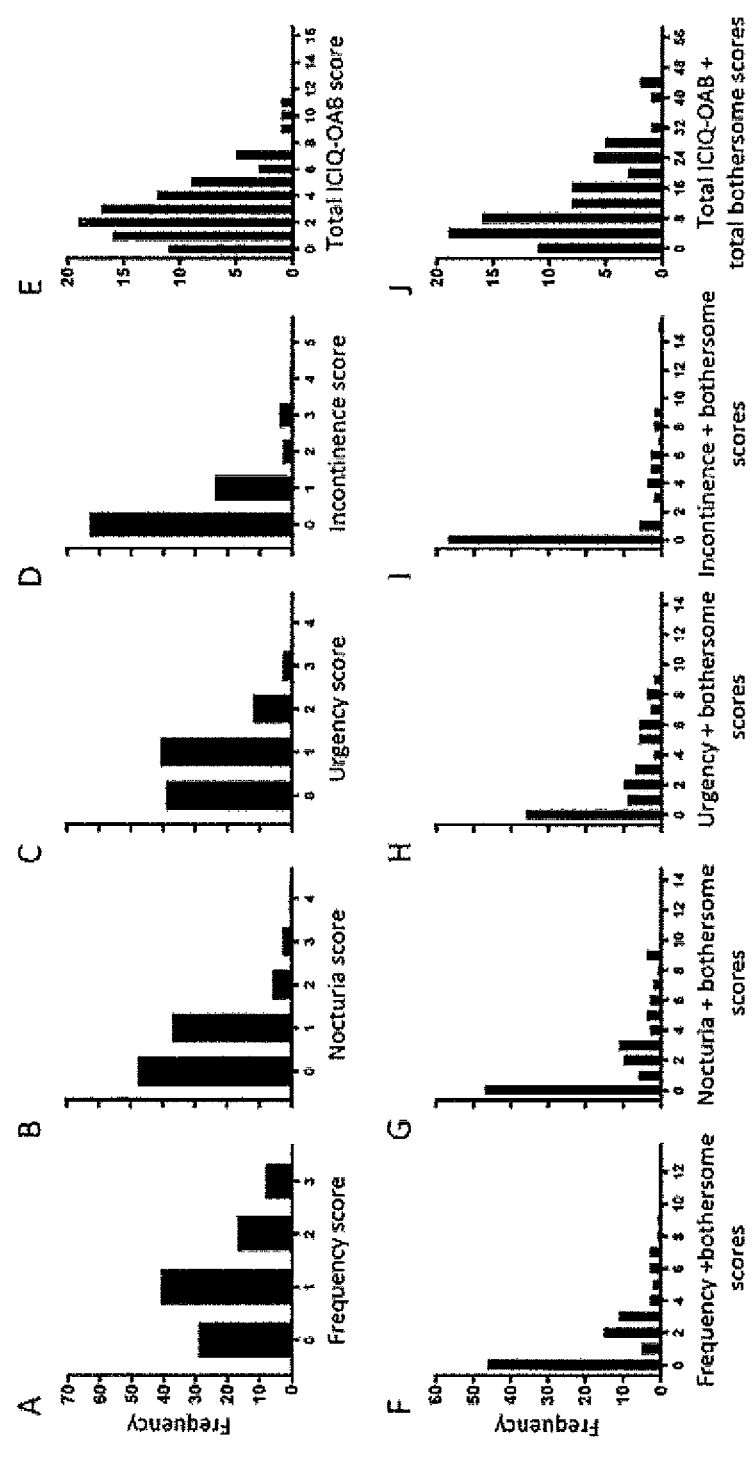
FIG. 2 shows frequency distributions of ICIQ-OAB urinary symptom scores and urinary symptoms' bothersome scores of eligible participants. (A-E) Frequency distributions (n=95) of ICIQ-OAB urinary symptom scores of eligible participants. (F-J) Frequency distributions (n=81) of ICIQ-OAB urinary symptoms plus bothersome score of eligible participants, 14 participants left one or some of the symptom associated bothersome questions blank. ICIQ-OAB=International consultation on incontinence questionnaire–overactive bladder.

The frequency distributions of urinary ICIQ-OAB characteristic scores of the eligible participants are shown in FIG. 2. The distributions of urinary symptom scores or urinary symptom scores plus associated bothersome scores were right-skewed and no apparent bimodal distribution, suggestive of two groups (OAB symptomatic and asymptomatic) was observed. Hence, the conventional total-score based diagnosis would not be appropriate for early-stage OAB diagnosis or grouping of the participants in this study.

Cluster Analysis

Two-step cluster analyses were performed on the participants' ICIQ-OAB urinary scores in order to identify any natural groupings (clusters). Two natural clusters were identified amongst participants based on the ICIQ-OAB questionnaire data (data not shown). All of the 95 eligible participants were included in the USSO based cluster analysis, whereas eighty one participants were included in the UBSO or USCPABS based analyses as 14 participants left one or some of the bothersome questions blank. Consequently, clusters formed based on USSO have higher statistical power to determine natural groupings compared to UBSO or USCPABS based analyses. Furthermore, cluster analysis identified urgency—key OAB symptom [Abrams et al. 2012]—as the main cluster predictor component in USSO based analysis. Therefore, the two clusters formed based on USSO were selected for biomarker profile assessments. Amongst 95 participants, 36 and 59 participants were assigned to clusters 1 and 2, respectively (Table 1). The distribution of urinary symptom scores amongst the two identified clusters are shown in Table 1. Participants in cluster 2 had statistically significant higher urinary symptom scores and were older compared to those in cluster 1 (Table 1). Therefore, cluster 1 was designated as 'OAB asymptomatic' and cluster 2 was designated as 'OAB symptomatic' for further analyses.

TABLE 1

Characterisation of clusters identified using two-step cluster analysis.

| Participant characteristic | Cluster 1 | Cluster 2 | P value |
|---|---|---|---|
| N | 36 | 59 | |
| Gender (F/M) | 20/16 | 41/18 | ns[a] |
| Age (yrs) | 54 (45.50-58.00)[b] | 59 (49.00-69.50) | 0.0079[c] |

TABLE 1-continued

Characterisation of clusters identified using two-step cluster analysis.

Figure 3:
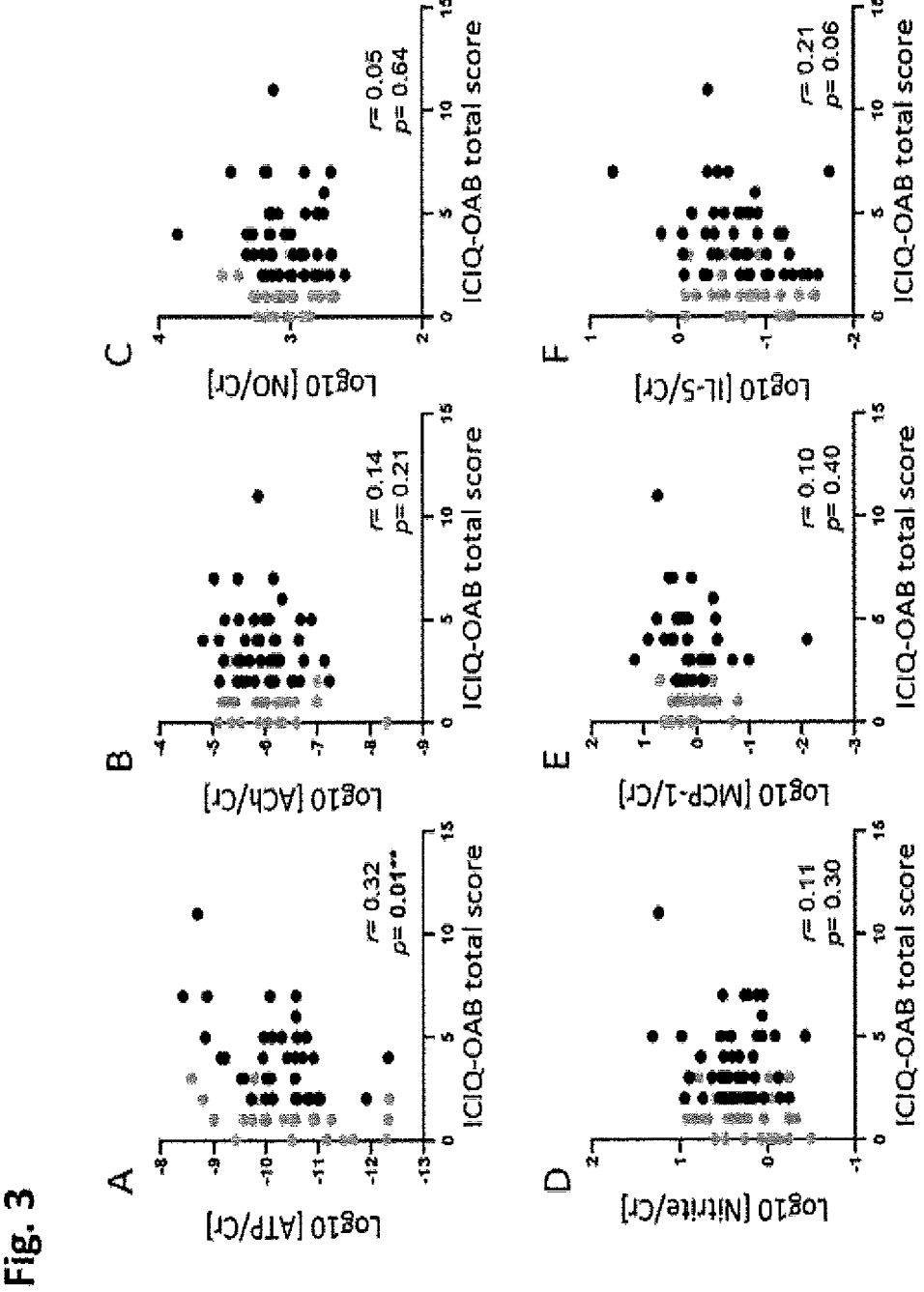
FIG. 3 shows the correlation between the urinary concentrations of candidate biomarkers and participants' total ICIQ-OAB urinary symptom scores. Cr=creatinine, all the urinary biomarker values were normalised to urinary creatinine concentrations; Grey circle=participants from OAB symptomatic cluster; Black circle=participants from OAB symptomatic cluster; r=Spearman r; p=p-value; **=significant p=value of $0.01\leq p\geq0.001$; Number format of y-axis=log.

| Participant characteristic | Cluster 1 | Cluster 2 | P value |
|---|---|---|---|
| U, median (IQR) | 0 (0.00-0.00) | 0.25 (0.25-0.37) | ≤0.0001[c] |
| I, median (IQR) | 0.0 (0.00-0.00) | 0.20 (0.00-0.20) | ≤0.0001[c] |
| F, median (IQR) | 0.33 (0.00-0.33) | 0.33 (0.33-0.67) | 0.0048[c] |
| N, median (IQR) | 0.00 (0.00-0.25) | 0.25 (0.00-0.25) | 0.0115[c] | n = number of participants in each cluster; ns = not significant; U = range standardised urgency symptom score (range: 0-1); I = range standardised incontinence symptom score (range: 0-1); F = range standardised frequency symptom score (range: 0-1); N = range standardised nocturia symptom score (range: 0-1); IQR = Interquartile range, 1$^{st}$ quartile-3$^{rd}$ quartile.
[a]= Z-test was used for comparison.
[b]= one missing age value, n = 35 for cluster 1
[c]= Mann-Whitney test Correlation Analysis FIG. 3 shows the relationship between the concentrations of the candidate urinary biomarkers (ATP, ACh, NO, Nitrite, MCP-1 and IL-5) and participants' total urinary symptoms scores. Positive trends were observed between the candidate biomarkers and participants' urinary symptom scores, and reached a statistically significant level with urinary ATP concentration (FIG. 3). The overlap of the concentrations of the candidate biomarkers between the asymptomatic and symptomatic groups further elucidated the inadequacy of a single biomarker as a diagnostic measure in those at early stages of OAB development (FIG. 3).

The correlation between the dependent variable (outcome i.e. OAB symptomatic) and the independent variables (i.e. participants' age, gender, total collected urine volume and urinary concentrations of ATP, ACh, NO, Nitrite, MCP-1 and IL-5) were summarised (data not shown). The correlation was only statistically significant with age (p value=0.008), which suggests that age may be a strong individual predictor of the outcome when subjected to logistic regression test. No multicollinearity (i.e. r value>0.80) was observed between the predictor variables, hence, all deemed to be suitable to be used simultaneously in logistic regression analyses.

Logistic Regression Analysis

Logistic regression analysis was used to assess whether a reliable OAB prediction equation could be developed by incorporating the candidate urinary biomarkers and participants' confounders. Initially, the power of each predicting parameter was assessed individually (data not shown). Amongst all the individual predicting parameters, age, as expected, was the only one that showed a statistically significant OAB prediction power over its null prediction model (Omnibus test p value=0.041, Table 2). In order to assess whether the addition of other predicting parameters would increase prediction ability of age, 20 combination models were developed by incorporating candidate urinary biomarkers and other confounders (data not shown). Amongst all the developed prediction models, seven (combinations 1, 10, 12, 14, 15, 17 & 18) were also shown to have statistically significant OAB prediction powers over their associated null models and were shown to have good fit (Omnibus test p values 0.05, HL test p value 0.05, Table 2).

TABLE 2

Prediction abilities of candidate biomarkers and participants' confounders assessed individually and in combination, using binary regression.

| | | | Logistic Regression parameters | | | |
| Predictive model | n | e | Pr Null model % | PR New model (%) | O test (p value) | HL test (p value) |
|---|---|---|---|---|---|---|
| Age | 94 | 2 | 62.80 | 61.70 | 0.041 | 0.060 |
| Combination 1 Age, Gender | 94 | 2 | 62.80 | 67.00 | 0.020 | 0.238 |
| Combination 10 Age, Gender, Il-5 | 81 | 15 | 60.50 | 66.70 | 0.011 | 0.677 |
| Combination 12 Age, Gender, ACh | 82 | 14 | 58.50 | 64.60 | 0.039 | 0.473 |
| Combination 14 Age, Gender, Il-5, ACh | 79 | 17 | 59.50 | 65.80 | 0.015 | 0.281 |
| Combination 15 Age, Gender, Il-5, ACh, ATP | 62 | 34 | 59.70 | 66.10 | 0.045 | 0.849 |
| Combination 17 Age, Gender, Il-5, ATP | 63 | 33 | 60.30 | 65.50 | 0.026 | 0.726 |
| Combination 18 Age, Gender, Il-5, NO | 81 | 15 | 60.50 | 66.70 | 0.024 | 0.550 | n = number participants included in analysis e = number participants excluded in analysis due to missing data; Null model = model with no predicting variable(s), just the intercept; Pr Null model (%) = percentage of cases for which the dependent variable was correctly predicted given the null model; New model = model with predicting variable(s); Pr New model (%) = percentage of cases for which the dependent variable was correctly predicted given the new model; O test-Omnibus Test of Model Coefficients assess whether the inclusion of predicting variable(s) will statistically improve the predicting ability of the new model over the null model, p ≤ 0.05 suggest (bold) statistically significant improvement in predicting ability of the new model null model. HL test-The Hosmer-Lemeshow goodness of fit test, a statistical test to assess goodness of fit for logistic regression models, ≥ 0.05 (bold) suggests model is a good fit.
* All the urinary biomarker values were normalised to urinary creatinine concentrations.

ROC Analysis and OAB Prediction Equations

Figure 4:
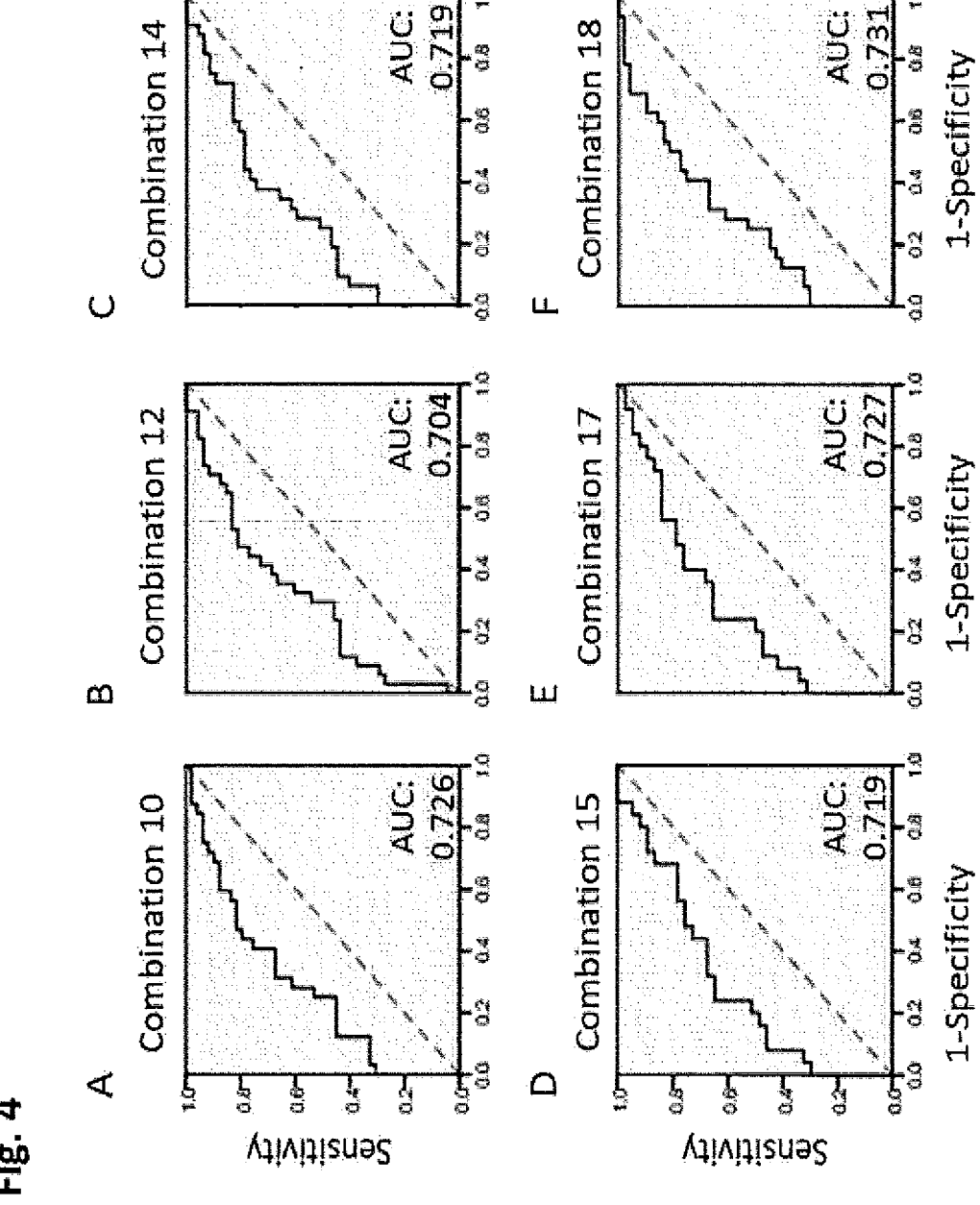
FIG. 4 shows receiver-operating characteristic curves (ROCs) of diagnostically reliable OAB prediction models. (A) Combination 10=Age+Gender+IL-5. (B) Combination 12=Age+Gender+ACh. (C) Combination 14=Age+Gender+IL-5+ACh. (D) Combination 15—Age+Gender+IL-5+

Discriminatory abilities of the eight prediction models with statistically significant OAB prediction abilities (significant Omnibus test p values, Table 2), were assessed by ROC analysis. Six prediction models (i.e. combinations 10, 12, 14, 15, 17 and 18) were shown to have clinically reliable diagnostic powers (Table 3, AUC≥0.7, ROC plots are shown in FIG. 4). Therefore, equations predicting likelihood of OAB were constructed for these six combinations (Table 4), whereby measuring urinary levels of the relevant biomarker(s) in each equation and entering the value(s) in the formula, the probability of someone having OAB (pOAB) could be calculated.

The optimal cut-off value of the predicted probability (pOAB) for each prediction equation was determined as the value with the maximum Youden Index (J) (Table 5). The sensitivity and specificity of each prediction equation at its optimal cut-off value is shown in Table 5. Subsequently, positive predictive value (PPV) and negative predictive value (NPV) of each OAB predictive equation was calculated based on the sensitivity and specificity at optimal cut-off value and based on an estimate of OAB prevalence of 20% [Irwin et al. 2011] (Table 5). Combination 17 predictive equation deemed to be the more reliable equation, considering both PPV (41%) and NPV (90%) values, compared to the other predictive equations (Table 5). In other words, by measuring the urinary concentrations of IL-5 and ATP and entering the Cr-normalised and standardised values in the combination 17 predictive equation alongside patient's age and gender, the pOAB can be calculated, and if pOAB>0.56 (pOAB cut-off for combination 17, Table 5) then a patient could be considered as having high risk of having/developing OAB. Considering the OAB prevalence of 20%, in real-world combination 17 predictive equation is capable of diagnosing 41% of patients with OAB and ruling out 90% of those without OAB, correctly. In general all the predictive equations had high NPV values (89-92%), meaning developed equations would be more suitable to rule out OAB than positively diagnosing it. Nevertheless, all the developed predictive equations showed to have higher PPV and NPV values compared to the current gold standard invasive tool that relies on the presence of DO for diagnosing those with OAB (Table 5, ΔPPV and ΔNPV).

TABLE 3

Discriminatory abilities of the selected prediction models were assessed by Receiver Operating Characteristic (ROC) analysis.

| Predictive model | AUC | SE | p value |
|---|---|---|---|
| Age | 0.633 | 0.056 | 0.008 |
| Combination 1 Age, Gender | 0.673 | 0.057 | 0.005 |
| Combination 10 Age, Gender, IL-5 | 0.726 | 0.056 | 0.001 |
| Combination 12 Age, Gender, ACh | 0.704 | 0.058 | 0.002 |
| Combination 14 Age, Gender, IL-5, ACh | 0.719 | 0.057 | 0.001 |
| Combination 15 Age, Gender, Il-5, ACh, ATP | 0.719 | 0.064 | 0.004 |
| Combination 17 Age, Gender, IL-5, ATP | 0.727 | 0.063 | 0.002 |
| Combination 18 Age, Gender, IL-5, NO | 0.731 | 0.056 | 0.000 |

AUC = area ROC curve; Bold value = AUC ≥ 0.70, meaning predictive model has clinically sufficient discriminatory power; SE = Standard error.

TABLE 4

OAB predictive equations.

| Predictive model | OAB prediction equation[a] Probability of having OAB ($p_{OAB}$) = $1/1 + e^{-x}$, where X = |
|---|---|
| Combination 10 | X = (−2.688 ± 1.050) + 5.472 ± 2.098 × subject's age + 1.356 ± 0.559 × Gender (Female = 1, Male = 0) + (−7.998 ± 40.273) × [IL-5/Cr] |
| Combination 12 | X = (−2.141 ± 0.966) + 4.506 ± 1.902 × subject's age + 1.034 ± 0.519 × Gender (Female = 1, Male = 0) + (−5294.063 ± 9075.456) × [ACh/Cr] |
| Combination 14 | X = (−2.825 ± 1.072) + 5.964 ± 2.167 × subject's age + 1.034 ± 0.519 × Gender (Female = 1, Male = 0) + 17.790 ± 58.762 × [IL-5/Cr] + (−9180.821 ± 12700.057) × [ACh/Cr] |
| Combination 15 | X = (−2.993 ± 1.197) + 5.580 ± 2.309 × subject's age + 1.724 ± 0.719 × Gender (Female = 1, Male = 0) + 63.571 ± 58.76273.444 × [IL-5/Cr] + (−10908.523 ± 13606.752) × [ACh/Cr] + (−566.991 ± 636.589) × [ATp/Cr] |
| Combination 17 | X = (−3.090 ± 1.200) + 5.393 ± 2.256 × subject's age + 1.797 ± 0.717 × Gender (Female = 1, Male = 0) + 34.767 ± 56.331 × [IL-5/Cr] + (−562.743 ± 629.316) × [ATP/Cr] |
| Combination 18 | X = (−2.650 ± 1.067) + 5.516 ± 2.120 × subject's age + 1.389 ± 0.583 × Gender (Female = 1, Male = 0) + (−4.060 ± 45.238) × [IL-5/Cr] + (−1.456 ± 6.833) × [NO/Cr] |

$p_{OAB}$ = probability of having OAB; e = exponential-e; Cr—Creatinine, urinary biomarker value needs to be normalised to creatinine concentrations before being entered in the equation.
[a] = values need to be range standardised to the reported value in Methods and Materials section before being entered in equation.

TABLE 5

Diagnostic characteristics of the constructed OAB predictive models.

| Predictive model | Based on maximum Youden Index (J) | | | Based on 20% prevalence of OAB | | | |
|---|---|---|---|---|---|---|---|
| | pOAB cut-off | Sensitivity (%) | Specificity (%) | PPV (%) | NPV (%) | | |
| Combination 10 | 0.51 | 67 | 69 | 35 | 89 | 5 | 3 |
| Combination 12 | 0.46 | 81 | 53 | 30 | 92 | 0 | 6 |
| Combination 14 | 0.46 | 74 | 63 | 33 | 91 | 3 | 5 |
| Combination 15 | 0.56 | 65 | 76 | 40 | 90 | 10 | 4 |
| Combination 17 | 0.56 | 66 | 76 | 41 | 90 | 11 | 4 |
| Combination 18 | 0.51 | 67 | 69 | 35 | 89 | 5 | 3 |
| Presence of DO[a] | | 54 | 68 | 30 | 86 | | |

$p_{OAB}$ = probability of having OAB; PPV Positive predictive value; NPV = Negative predictive value; ΔPPV = (PPV of predictive model) − (PPV of Urodynamic); ΔNPV = (NPV of predictive model) − (NPV of Urodynamic).
[a] Sensitivity and specificity values for urodynamic test was obtained from Digesu etal. 2003 study where the presence of DO was use as a marker for diagnosing those presenting with OAB symptoms.

CONCLUSION

This analysis elucidated six combinations, with clinically reliable diagnostic power to distinguish participants with or without early-stage OAB (Table 2 and FIG. 4). Predictive equations for all six combinations had high NPV values (89-92%) but relatively lower PPV values (30-41%); meaning that they are better suited to rule out OAB. The performance of these combinations is similar to other urine-based tests for other disease e.g. bladder carcinoma [Valenberg et al. 2018] or prostate cancer [Lughezzani et al. 2018]. This means that by measuring the urinary levels of the associated biomarker(s) in each equation and entering the value(s) in the formula, these novel equations would enable healthcare professionals to predict the probability of someone having OAB at much earlier stage in its development and more accurately than the current invasive means of urodynamically-observed DO (Table 5), but more importantly would enable them to accurately and non-invasively exclude OAB in those patients with aetiologically distinct diseases which have overlapping symptoms with OAB.

REFERENCES

Abrams P, Chapple C R, Jünemann K P, Sharpe S. Urinary urgency: a review of its assessment as the key symptom of the overactive bladder syndrome. World J Urol. 2012 June; 30(3):385-92.

Abrams P, Cardozo L, Wagg A, Wein A. (Eds) Incontinence 6th Edition (2017). ICI-ICS. International Continence Society, Bristol UK, ISBN: 978-0956960733.

Digesu G A, Khullar V, Cardozo L, Salvatore S. Overactive bladder symptoms: do we need urodynamics? Neurourology and Urodynamics. 2003; 22:105-8.

Hashim H, Abrams P. Is the bladder a reliable witness for predicting detrusor overactivity? The Journal of Urology. 2006; 175:191-4.

Irwin D E, Kopp Z S, Agatep B, Milsom I, Abrams P. Worldwide prevalence estimates of lower urinary tract symptoms, overactive bladder, urinary incontinence and bladder outlet obstruction. BJU Int. 2011; 108:1132-8.

Lughezzani G, Saita A, Lazzeri M et al (in press). Comparison of the Diagnostic Accuracy of Micro-ultrasound and Magnetic Resonance Imaging/Ultrasound Fusion Targeted Biopsies for the Diagnosis of Clinically Significant Prostate Cancer. Eur Urol. (in press).

Valenberg F J P V, Hiar A M, Wallace E, et al. Prospective Validation of an mRNA-based Urine Test for Surveillance of Patients with Bladder Cancer. Eur Urol. (in press).

The invention claimed is:

1. A method of diagnosing overactive bladder disorder (OAB), the method comprising:

measuring the concentrations of one or more of adenosine triphosphate (ATP), acetylcholine (ACh), nitric oxide (NO) and interleukin 5 (IL-5) in a sample obtained from a subject;

normalising the concentrations to the concentration of creatinine (Cr) in the sample;

range standardising the normalised concentrations and age of the subject to the following values: Age to 120 years old; ATP/Cr to 0.000001; ACh/Cr to 0.1; NO to 20000; IL-5/Cr to 100;

wherein the likelihood of having OAB (pOAB)=1/(1+e^(-x)), where X=one or more of the following:

(−2.688±1.050)+5.472±2.098×subject's age+1.356-0.559×Gender (Female=1, Male=0)+(−7.998±40.273)×[IL-5/Cr];  (a)

(−2.141±0.966)+4.506±1.902×subject's age+1.034±0.519×Gender (Female=1, Male-0)+(−5294.063±9075.456)×[ACh/Cr];  (b)

(−2.825=1.072)+5.964±2.167×subject's age+1.312±0.562×Gender (Female=1, Male=0)+17.790±58.762×[IL-5/Cr]+(−9180.821±12700.057)×[ACh/Cr];  (c)

(−2.993±1.197)+5.580±2.309×subject's age+1.724-0.719×Gender (Female=1, Male-0)+63.571±73.444×[IL-5/Cr]+(−10908.523±13606.752)×[ACh/Cr]+(−566.991±636.589)×[ATP/Cr];  (d)

(−3.090±1.200)+5.393±2.256×subject's age+1.797±0.717×Gender (Female=1, Male=0)+34.767±56.331×[IL-5/Cr]+(−562.743±629.316)×[ATP/Cr]; or  (e)

(−2.650±1.067)+5.516±2.120×subject's age+1.389-0.583×Gender (Female=1, Male=0)+(−4.060±45.238)×[IL-5/Cr]+(−1.456=6.833)×[NO/Cr];  (f)

wherein a calculated pOAB value above a first threshold indicates that the subject has a high likelihood of having or developing OAB, and wherein the calculated pOAB value below a second threshold indicates that the subject does not have OAB;

diagnosing the subject with OAB, based on the calculated pOAB value that indicates OAB; and administering a therapeutic agent to the subject diagnosed as having OAB, wherein the therapeutic agent is an antimuscarinic drug or a β3 adrenergic receptor agonist, wherein the antimuscarinic drug is selected from one or more of darifenacin, oxybutynin, tolterodine, solifenacin, trospium, flavoxate, propiverine or fesoterodine, and wherein the β3 adrenergic receptor agonist is mirabegron.

2. The method of claim 1, wherein at least one of the first threshold or the second threshold is 0.5.

3. The method of claim 1, wherein the sample is a urine sample.

4. The method of claim 1, wherein the concentrations of any of ATP, ACh, NO, IL-5 or Cr are measured using an antibody-based platform or an RNA aptamer-based platform or a combination thereof.

5. A method of monitoring the progression of OAB, the method comprising calculating first pOAB values and second pOAB values according to the method of claim 1, wherein the first pOAB values and the second pOAB values are obtained from first samples and second samples obtained from the subject having or suspected of having OAB.

6. The method of claim 5, wherein the first samples and the second samples are obtained at an interval of at least two weeks.

* * * * *